(12) United States Patent
Cai et al.

(10) Patent No.: US 8,691,576 B2
(45) Date of Patent: Apr. 8, 2014

(54) **REGENERATION AND MASS PROPAGATION OF *JATROPHA CURCAS* THROUGH SOMATIC EMBRYOGENESIS**

(75) Inventors: Lin Cai, Singapore (SG); Lianghui Ji, Singapore (SG)

(73) Assignee: Joil (S) Pte Ltd., Singapore (SG)

( * ) Notice: Subject to any disclaimer, the term of this patent is extended or adjusted under 35 U.S.C. 154(b) by 763 days.

(21) Appl. No.: 12/863,698

(22) PCT Filed: Jan. 7, 2009

(86) PCT No.: PCT/SG2009/000015
§ 371 (c)(1),
(2), (4) Date: Jul. 20, 2010

(87) PCT Pub. No.: WO2009/096900
PCT Pub. Date: Aug. 6, 2009

(65) Prior Publication Data
US 2010/0304488 A1      Dec. 2, 2010

Related U.S. Application Data

(60) Provisional application No. 61/025,430, filed on Feb. 1, 2008.

(51) Int. Cl.
*C12N 5/00*     (2006.01)
*C12N 5/02*     (2006.01)

(52) U.S. Cl.
USPC ........................................................... 435/420

(58) Field of Classification Search
USPC ........................................................... 435/420
See application file for complete search history.

(56) References Cited

U.S. PATENT DOCUMENTS 7,005,298 B1 * 2/2006 Saxena et al. ................. 435/420

FOREIGN PATENT DOCUMENTS

WO      2008/012832 A2    1/2008

OTHER PUBLICATIONS

Sujatha, M. and Reddy Papi. "Morpogenic responses of *Jatropha integerrima* explants to cytokinins" (Abstract) Biologia (Bratislava) 55 (1) pp. 99-104 Feb. 2000.*
Soomoro R and RA Memon. "Establishment of Callus and Suspension Culture in *Jatropha curcas*." (Abstract) Pakistan Journal of Botany V. 39 N7, SI pp. 2431-2441 Dec. 2007.*
Pletsch, Marcia and Barry V. Charlwood. "Accumulation of diterpenoids in cell and root-organ cultures of *Jatropha* species." Journal of Plant Physiology. vol. 150, Issues 1-2 1997, pp. 37-45.*
Sujatha, M. and Mukta Dhingra. "Rapid plant regeneration from various explants of *Jatropha integerrima*" Plant Cell, Tissue and Organ Culture 35: 293-296 1993.*
Compton et al. "Use of protoplasts for plant improvement" in Trigiano and Gray "Plant Tissue Culture Concepts and Laboratory Exercises" CRC Press 1996. see p. 206.*

(Continued)

*Primary Examiner* — Wendy C Haas
(74) *Attorney, Agent, or Firm* — Rothwell, Figg, Ernst & Manbeck P.C.

(57) ABSTRACT

The present invention relates to the field of somatic embryo production, particularly to methods for the regeneration of *Jatropha* through somatic embryogenesis. More specifically, the present invention relates to a method and media compositions for regeneration of plants of *Jatropha curcas*. The method is well suited for *Jatropha curcas* transformation and for producing clonal planting stock useful for large scale *Jatropha curcas* plantation.

26 Claims, 6 Drawing Sheets

(56) References Cited

OTHER PUBLICATIONS

Sujatha, M. et al., "Role of biotechnological interventions in the improvement of castor (*Ricinus communis* L.) and *Jatropha curcas* L.," Biotechnology Advances, Elsevier Publishing, Barking, GB, vol. 26, No. 5, Sep. 1, 2008, pp. 424-435.

Rajore, S. et al., "An alternative source for regenerable organogenic callus induction in *Jatropha curcas* L.," Indian Journal of Biotechnology, National Institute of Science Communications, New Delhi, IN, vol. 6, Oct. 1, 2007, pp. 545-548.

Thepsamran, N. et al., "In vitro multiple shoot induction of physic nut (*Jatropha curcas*)," In Vitro Multiple Shoot Induction of Physic Nut (*Jatropha curcas*), Department of Biology, Silpakorn Univ, Thailand, (Online), Jan. 1, 2006.

Kalimuthu, K. et al., "In vitro propagation of the biodiesel plant *Jatropha curcas* L.", Plant Tissue Culture & Biotechnology, 2007, vol. 17, No. 2, pp. 137-147.

Jha, T.B. et al., "Somatic embryogenesis in *Jatropha curcas* Linn., an important biofuel plant", Plant Biotechnology Reports, 2007, vol. 1, No. 3, pp. 135-140.

Sardana, J. et al., "An expeditious method for regeneration of somatic embryos in *Jatropha curcas* L.," Phytomorphology, 2000, vol. 50, No. 3 & 4, pp. 239-242.

Krit, J.J.M. et al., "Direct cyclic somatic embryogenesis of Cassava for mass production purposes", Methods in Molecular Biology, vol. 111:Plant Cell Culture Protocols, Ed: R.D. Hall, Humana Press Inc., Totawa, NJ, pp. 61-70.

Bhojwani, S.S. and Razdan, M.K., "Suspension Cultures", In: Developments in Crop Science vol. 5, Plant tissue Culture: Theory and Practice, Elsevier Amsterdam—Oxford—New York—Tokyo 1983, pp. 46-52.

\* cited by examiner

REGENERATION AND MASS PROPAGATION OF *JATROPHA CURCAS* THROUGH SOMATIC EMBRYOGENESIS

CROSS-REFERENCE TO RELATED APPLICATION

The present application is a national stage filing under 35 U.S.C. §371 of PCT/SG2009/000015, filed 7 Jan. 2009 and claims the benefit of and priority to U.S. Provisional Patent Application Ser. No. 61/025,430, filed on 1 Feb. 2008, each application is incorporated herein by reference in its entirety.

BACKGROUND OF THE INVENTION

The present invention relates to the field of somatic embryo production, particularly to methods for the regeneration of *Jatropha* through somatic embryogenesis. More specifically, the present invention relates to a method and media compositions for regeneration of plants of *Jatropha curcas*. The method is well suited for *Jatropha curcas* transformation and for producing clonal planting stock useful for large scale *Jatropha curcas* plantation.

The publications and other materials used herein to illuminate the background of the invention or provide additional details respecting the practice, are incorporated by reference, and for convenience are respectively grouped in the Bibliography.

The world is facing dwindling supply is fossil fuel and worsening Green House Effect. There is an urgent demand to increase production and consumption of renewable energy. Biofuels have been recognized as a national priority for many countries in their search for alternative sources to meet their energy security needs and at the same time help reduce $CO_2$ emissions that cause the Green House Effect. The demand for biofuel has put increasing pressure on food production. For example, to satisfy the biofuel need for Germany in 2017 as mandated by the German government the entire farm land of this country would have to be used for growing bioenergy crops with no land left for food production. To ease this competition for land and to satisfy our need for renewable fuels, there is a strong need to utilize marginal land for bioenergy production.

*Jatropha curcas* is a small woody plant belonging to the Euphorbiaceae family. Several unique characters of *Jatropha curcas* make it an ideal plant for biodiesel production. These include the ability to grow on marginal land; low requirement for water; a non-food crop status; fast oil production in 1-2 years after planting compared to more than 3 years for oil palm. Accordingly, the Indonesian government has announced that they will dedicate about 3 million hectares of land for *Jatropha* planting in the next 5 years.

Amongst the various countries, India is the most advanced in terms of establishment of *Jatropha* plantations. However, the seed yield of an Indian *Jatropha* plantation remains low, ranging from 0.4 to 12 MT/Ha (compared with about 19Mt/Ha for palm). This difference is at least in part attributed to the lack of research in breeding and farm management in *Jatropha curcas*.

The intense interest in oil from *Jatropha curcas* has generated enormous pressure to supply enough seeds that are homogenous and productive enough for plantation. Therefore, there is an urgent need to mass propagate elite trees. Equally urgent are methods to improve various agronomical traits of *Jatropha curcas*. Genetic engineering is recognized as a fast method for crop improvement. Plant transformation is essentially a two step process, i.e., delivery of genes into a host cell followed by regeneration of the transformed cell into a plant. Somatic embryogenic calli or somatic embryogenic suspension cultures is generally regarded as the most efficient method of regeneration as most of the transformed cells have already acquired the embryogenic potential that will drive them to develop into a somatic embryo quite spontaneously, a process similar to a fertilized egg cell in a zygotic embryo (Dodeman, et al., 1997).

Somatic embryos are suitable for transformation via *Agrobacterium tuniefaciens* (Mathews et al., 1992), microinjection (Neuhaus et al., 1987) and particle bombardment (Wilde et al., 1992). In addition, somatic embryos or somatic embryogenic calli can be cryopreserved using liquid nitrogen without loss of viability. This they are ideal materials for maintenance of germplasm as well as cell embryogenecity.

Somatic embryos are clonal in origin and thus multiplication using somatic embryos can have the potential for exceedingly high rates of vegetative increase and is therefore of considerable commercial interest. Regeneration via somatic embryogenesis is an attractive option for plant tissue culture. Somatic embryos reportedly provide more stable regenerants than shoots. Another advantage of regeneration systems using somatic embryos is their apparent single cell origin. This means that it is unlikely that regenerants are of chimerical origin, since, if a regenerant originates from a cluster of cells rather than a single sell, the plant tissues may be chimerical or unstable and produce off-types. Somatic embryogenesis has also been used successfully to mass propagation a number of plant species, e.g., banana and pines (Cote et al., 2000; Merkle and Dean, 2000). Somatic embryos may be made into synthetic seeds which reduce transportation cost and competition of seeds for oil (Conrad™, 1996).

To date, a large number of protocols for somatic embryogenesis have been developed. Some examples include the following: Eudes et al. (2006) (Pooidaea); Kasha and Simion (2001, 2004) (cereal plant); Xie and Hong (2004) (*Acacia mangium*); Guiltinan et al. (2001) (cacao); Trolinder et al. (1999) (cotton); Rutter et al. (1998a, 1998b) (coniferous plants); Handley and Levis (1998) (coniferous plants); Chee (1991, 1997) (squash); Becwar et al. (1995, 1996) (coniferous plants); Genovesi and Yingling (1995) (maize); Collins et al. (1991) (Glycine species); Cooley and Wilcox (1987) (sunflower); Schoofs et al. (1998) (banana); Jouenne et al. (1995) (grape); Garay et al. (2003) (agave tequilana weber); Sondahl et al. (1993) (Cacao); Armstrong and Deboer (2000) (cotton); Tuli and Mithilesh (2005) (cotton); Seabrook and Douglas (1999) (potato); Buffard-Morel et al. (1994) (coconut palm) and Cai and Ji (2005) (cotton). As illustrated in this art, various explants can be used. However, there is no culture media, culture conditions and regeneration procedures that are universally applicable. For example, Fki, et al. (2003) describes a protocol for date palm (*Phoenix dactylifera*) using immature florescences in which somatic embryogenesis (friable calli) was initiated on MS media supplemented with high concentration of 2,4-dichlorophenoxyacetic acid (2,4-D) (10 mg/l), 30 mg/l adenine, 100 mg/l glutamine, 2 mg/l glycine, 30 mg/l Fe-EDTA, 100 mg/l $KH_2PO_4$, 100 mg/l myo-inositol and further embryos progression was achieved by reducing 2,4-D to 1 mg/l in either solid or liquid medium. In contrast, Cai and Ji (2005) disclose initiation of somatic embryogenesis of cotton calli, which is induced from root explants in a much simpler medium with very low concentration of 2,4-D and kinetin (0.05 mg/l 2,4-D and 0.1 mg/l kinetin), by exposing them in hormone-free, high nitrate medium after the calli initiation. In addition, dramatic changes may be found even between cultivars of the same species.

Research on somatic embryogenesis of *Jatropha curcas* has been very limited. Recently, preliminary results on somatic embryogenesis of *Jatropha curcas* using leaf tissues was reported (Ma et al., 2007). Although the author was successful in inducing somatic embryogenesis using a combination of kinetin and indolebutyric acid (IBA), less than 2% of the somatic embryos were able to convert into viable plants. Furthermore, the complete sexual life cycle using the method remains to be demonstrated. Notably, we have not been able to induce somatic embryogenesis in *Jatropha curcas* using the same protocol and explants despite trying three germplasm collections, including one from India.

Thus, there is a need for methods of somatic embryogensis and preparation of embryogenic liquid suspension cultures from which high efficiency plant regeneration and production of sexually fertile *Jatropha curcas* plants can be achieved.

SUMMARY OF THE INVENTION

The present invention relates to methods for regeneration in vitro of plants in the genera of *Jatropha*, more specifically, in *Jatropha curcas* and its artificial hybrids. More specifically, the present invention relates to method of somatic embryogensis and preparation of embryogenic liquid suspension cultures from which high efficiency plant regeneration and production of sexually fertile *Jatropha curcas* plants are be achieved. These methods also enable high efficiency transformation of this plant.

In one aspect, the present invention provides a method for producing somatic embryos from explants obtained from zygotic embryos of *Jatropha curcas*. In accordance with this aspect, the explants are placed on a solid medium containing an auxin. Cytokinins can be optionally supplemented at low concentration. Many known media, such as combinations of MS salts, B5 salts and FNL salts with either MS vitamins or B5 vitamins, are effective for this method. The somatic embryos thus induced are usually present as 1-2 separate embryos of similar size and are referred to herein as Type I somatic embryos (TISEs). Under high auxin concentrations, secondary somatic embryos may be produced from TISEs. TISEs may be germinated directly if the original medium contains low concentration of auxin. Alternatively, they may be matured on a second medium with no hormone and optionally supplemented with amino acids. Germination of somatic embryos can be improved with giberellic acid ($GA_3$) in ½ or ¼ strength MS or B5 media. The germinated embryos can be further developed in a medium for 2-6 weeks before transplanted to soil pots.

In a second aspect, the present invention provides method for producing somatic embryos and embryogenic calli. In accordance with this aspect, a two-step induction process is used, wherein explants are excised from zygotic embryos and cultured in a first solid medium comprising an auxin. Cytokinins can be optionally added. The explants thus induced are transferred to a second solid medium 2-6 weeks later, preferably 2-4 weeks later. The second solid medium is hormone-free and optionally supplemented with amino acids. Many known media, such as MS salts, B5 salt or FNL salt in conjunction with either MS vitamins or B5 vitamins, are effective in inducing somatic embryos, which are usually present as a cluster with more than 5 embryos of various sizes and are referred to herein as Type II Somatic Embryos (TIISEs). The TIISEs may multiply as embryogenic calli. These materials are ideal for plant propagation and transformation. The matured somatic embryos are preferably germinated in a medium with $GA_3$ in ½ or ¼ strength medium, for example, MS salts with MS vitamins. The germinated plantlets may be further developed in a medium before transplanted to soil pots.

In a third aspect, the present invention provides a method for preparing embryogenic liquid suspension cultures. In accordance with this aspect, embryogenic calli or TIISEs prepared as described above are transferred to a liquid medium and subcultured regularly, usually every 2-3 weeks. The liquid medium can be one of combinations of MS salts, B5 salts and FNL salts with either MS vitamins or B5 vitamins. Amino acids are preferably supplemented in the liquid medium. Auxins are preferably included in the medium. Somatic embryos larger than 0.5 cm long are preferably removed by sieving during subcultures. The cultures are maintained in a shaking platform with 16 hours lighting. The liquid culture system is well suited for preparation a large batch of synchronized somatic embryos, which can be used for plant propagation and as explants for genetic transformation.

In a fourth aspect, the present invention provides a method for culturing certain somatic embryo stages to reinitiate the embryogenic development pathway. In accordance with this aspect, a fraction of the somatic embryos that continue to mature to stages not suitable for initiation of new embryogenic calli in the liquid medium are further cultured on a solid medium with high concentration of auxin followed by shifting to a hormone-free solid medium that is further supplemented with free amino acids. This aspect of the invention is a practical supplement to the liquid suspension culture system to provide large amount of explants for genetic transformation.

In a fifth aspect, the present invention provides a method of maintaining the liquid suspension culture so that the amount of callus tissue is increased and the germination of embryos is inhibited. In accordance with this aspect, somatic embryogenic callus tissue is maintained in suspension culture in a liquid maintenance medium and subcultured regularly, usually every 2-3 weeks. The liquid maintenance medium is preferably a $NH_4NO_3$-free medium that contains MS salts and B5 vitamins. Other media such as B5 salts with B5 vitamins, or FNL salts with B5 vitamins could also be used albeit with a substantially poorer result. Amino acids are preferably supplemented in the liquid medium. Auxins are preferably included in the medium. The liquid medium is further supplemented with polyethylene glycol (PEG). Culturing in the liquid maintenance medium provides an increase in the mass of the callus tissue. This callus tissue is maintained more uniformly at globular stage or torpedo stage. The medium inhibits the germination of the embryos.

The methods of the present invention comprise a complete and efficient system which can be used for regeneration of plants in the genera of *Jatropha*, more specifically in the *Jatropha curcas* species and its artificial hybrids. Numerous somatic embryos have been produced by this system and the regenerants have been demonstrated to be completely normal in vegetative development and sexual preproduction.

BRIEF DESCRIPTION OF THE FIGURES

FIG. 1A: Somatic embryo initiated from 0.6 cm-long cotylendon after culturing for 40 days in a medium with 5 mg/l 2,4-D and 0.1 mg/l kinetin. FIG. 1B: Somatic embryos and secondary somatic embryos originated from endosperm-hypocotyl junction. The explant was cultured for 70 days in a medium with 0.2 g/l 2,4-D and 0.1 mg/l kinetin. FIG. 1C: TISEs originated from endosperm explant of a 1.5 cm-long zygotic embryo that had been cultured for 40 days in a medium with 0.2 g/l 2,4-D and 0.1 g/l kinetin. FIG. 1D: TISE originated from the endosperm-hypocotyl junction. The explant was cultured for 21 days in a medium with 0.2 g/l 2,4-D and 0.1 g/l kinetin.

FIG. 3A: Somatic embryos germinated in G13 medium for one month. FIG. 3B: A plantlet further developed in ½ strength MS medium (with 15 g/l sucrose) for one month. FIG. 3C: A *Jatropha curcas* plant regenerated from a TIISE. FIG. 3D: Close-up view of FIG. 3C showing the flowers. FIG. 3E: Close-up view of FIG. 3C showing the maturing fruits.

FIG. 4A: No glutamine, 0.25 g/l asparagine. FIG. 4B: No glutamine, 0.25 g/l asparagine and $KNO_3$ increased to 2.85 g/l. FIG. 4C: 0.5 g/l glutamine, 0.25 g/l asparagine. FIG. 4D: Enlarged view of FIG. 4C (framed region), showing abundant production of secondary embryos and formation of embryogenic calli. Scale bar in D represent 1 cm.

FIG. 5A: 20 g/l sucrose, 1 g/l glutamine, 0.5 g/l asparagine, no 2,4-D. FIG. 5B: 20 g/l sucrose, 1 g/l glutamine, 0.5 g/l asparagine, 0.2 g/l 2,4-D. FIG. 5C: 30 g/l sucrose, 1 g/l glutamine, 0.5 g/l asparagine, 0.2 g/l 2,4-D. FIG. 5D: 20 g/l sucrose, 1 g/l glutamine, 0.5 g/l asparagine, 1 g/l 2,4-D. Arrow indicates the non-embryogenic ball-shaped calli. Scale bar represents 1 cm.

DETAILED DESCRIPTION OF THE INVENTION

Figure 1A:
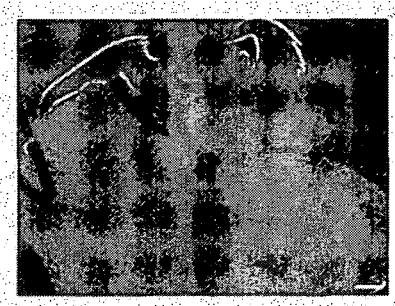
FIGS. 1A-1D show Type I somatic embryo (TISE) formation. All explants were cultured in media with MS salts, B5 medium, 2.2 g/l phytagel, pH5.8. Hormone level varied. The scale bar indicates 1 mm.
Figure 1B:
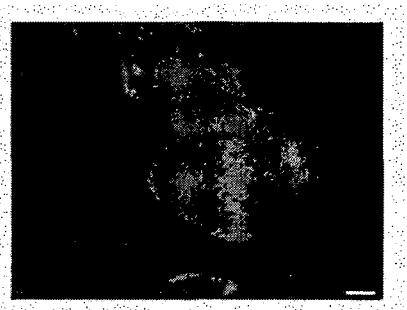
Figure 1C:
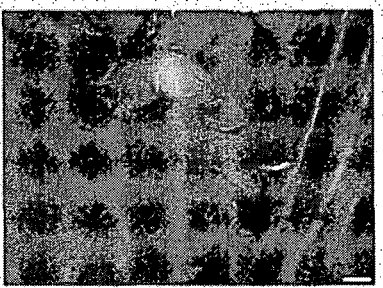
Figure 1D:
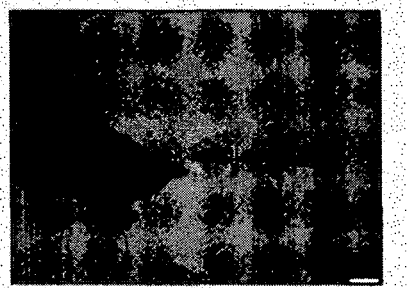

The present invention relates to the field of somatic embryo production, particularly to methods for the regeneration of *Jatropha* through somatic embryogenesis. More specifically, the present invention relates to a method and media compositions for regeneration of plants of *Jatropha curcas*. The method is well suited for *Jatropha curcas* transformation and for producing clonal planting stock useful for large scale *Jatropha curcas* plantation.

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. Finally, high efficiency transformation of plants can be accomplished using somatic embryogenesis to regenerated transformed cells.

In one aspect of the present invention, somatic embryos are produced by inducing somatic embryo formation on explant tissue. In one embodiment, somatic embryos are induced from explants obtained from zygotic embryos of a plant of the genera *Jatropha*. In accordance with this embodiment, the explants are placed on a solid medium containing an auxin. Preferably, the explants are endosperm tissue detached from zygotic embryos. The zygotic embryos have a length that is from about 0.3 cm to about 1.5 cm, preferably from about 0.5 cm to about 1.5 cm and more preferably from about 0.5 cm to about 1.0 cm. In one embodiment, an auxin that is effective in inducing somatic embryos in such tissues is 2,4-D in a wide range of concentration, for example from about 0.1 mg/l to about 20 mg/l, preferably from about 1.0 mg/l to about 5 mg/l. The medium can optionally be supplemented with a cytokinin at low concentration. In one embodiment, a cytokinin that can be included is kinetin at a concentration of, for example, from about 0.05 mg/l to about 1 mg/l. Many known media can be used as the solid medium and are effective for this aspect of the invention. Examples of suitable media include combinations of MS salts, B5 salts or FNL salts with either MS vitamins or B5 vitamins. In one embodiment, the auxin-containing medium is devoid of $NH_4NO_3$. In one embodiment, the explants are cultured in the dark. In another embodiment, the explants are cultured with a light and dark phase. The somatic embryos thus induced are usually present as 1-2 separate embryos of similar size and are referred to herein as Type I somatic embryos (TISEs). Under high auxin concentrations, for example from about 1.0 mg/l to about 5 mg/l, secondary somatic embryos may be produced from the TISEs. The TISEs produced in accordance with this aspect of the invention can be germinated directly, if the original medium contains low concentration of auxin, such as 2,4-D, for example, from about 0.1 mg/l to about 1.0 mg/l 2,4-D.

Alternatively, the TISEs can be matured on a second medium that contains no hormone and is supplemented with one or more amino acids. In one embodiment, the amino acid is glutamine, asparagine or a combination of glutamine and asparagine. In one embodiment, the concentration of glutamine in this maturation medium can be, for example from about 0.25 g/l to about 2 g/l, preferably from about 0.5 g/l to about 1.0 g/l and more preferably from about 0.5 g/l to about 0.75 g/l. In one embodiment, the concentration of asparagine in this maturation medium can be, for example from about 0.1 g/l to about 1 g/l, preferably from about 0.1 g/l to about 0.75 g/l and more preferably from about 0.25 g/l to about 0.5 g/l. In another embodiment, the amino acids are casein hydrolysate. The concentration of casein hydrolysate in this maturation medium can be, for example, from about 50 mg/l to about 1,000 mg/l, preferably from about 100 mg/l to about 500 mg/ml and more preferably from about 100 mg/l to about 200 mg/l.

The somatic embryos are then transferred to a medium for germination. Germination of somatic embryos can be improved with giberellic acid ($GA_3$) using a medium that is ½ or ¼ strength MS or B5 media. In one embodiment, the concentration of $GA_3$ is, for example from about 0.5 mg/l to about 10 mg/l, preferably from about 1 mg/l to about 5 mg/l and more preferably from about 2 mg/l to about 3 mg/l. The germinated embryos can be further developed in this medium for 2-6 weeks before transplanted to soil pots. The use of gelling agents, such as agar and phytagen, for preparing solid media is well known in the art. In one embodiment, the preferred gelling agent is phytagel. In this embodiment, the amount of phytagel is, for example, between about 2.2 g/l and 2.8 g/l.

In a second aspect of the present invention, somatic embryos are produced by a two-step induction process to induce somatic embryo formation from explant tissue of the genera *Jatropha*. In accordance with this aspect, explants are cultured in a first medium containing an auxin. In one embodiment, the explants are excised from zygotic embryos. The zygotic embryos have a length that is from about 0.3 cm to about 1.5 cm, preferably from about 0.5 cm to about 1.5 cm and more preferably from about 0.5 cm to about 1.0 cm. In a second embodiment, explants are excised from post-torpedo stage somatic embryos. In one embodiment, the explants from either the zygotic embryos or the post-torpedo stage somatic embryos are hypocotyl tissue or root apex tissue. In one embodiment, an auxin that is effective in inducing somatic embryos in such tissues is 2,4-D in a range of concentration, for example from about 0.5 mg/l to about 10 mg/l, preferably from about 2 mg/l to about 5 mg/l. The medium can optionally be supplemented with a cytokinin at low concentration. In one embodiment, a cytokine that can be included is kinetin at a concentration of, for example, between about 0.05 mg/l to about 1 mg/l. The explants are cultured on the auxin-containing medium for a period of time sufficient to initiate embryogenic calli. In one embodiment, the culturing on the auxin-containing medium is for about 1 week to about 8 weeks, preferably from about 2 weeks to about 6 weeks and more preferably from about 2 weeks to about 4 weeks.

The embryogenic calli and/or explants are then transferred to a second solid medium for maturation. The second solid medium is hormone-free and supplemented with one or more amino acids. In one embodiment, the amino acid is glutamine, asparagine or a combination of glutamine and asparagine. In one embodiment, the concentration of glutamine can be, for example, from about 0.2 g/l to about 2 g/l, preferably from about 0.2 g/l to about 1.5 g/l and more preferably from about 0.5 g/l to about 1.0 g/l. In one embodiment, the concentration of asparagine can be, for example, from about 0.1 g/l to about 1.5 g/l, preferably from about 0.2 g/l to about 1.0 g/l and more preferably from about 0.25 g/l to about 0.5 g/l. In another embodiment, the amino acids are casein hydrolysate. The concentration of casein hydrolysate in this medium can be, for example, from about 50 mg/l to about 1,000 mg/l, preferably from about 100 mg/l to about 500 mg/ml and more preferably from about 100 mg/l to about 200 mg/l. In one embodiment, the second medium (i.e., the hormone free medium) is devoid of $NH_4NO_3$. In one embodiment, the second medium may also contain a source of carbohydrate to improve somatic embryo maturation. In one embodiment the carbohydrate can be sucrose and/or maltose. Sucrose can be present in an amount from about 10 g/l to about 20 g/l. Maltose can be present in an amount from about 20 g/l to about 60 g/l. Many known media can be used for each of the solid medium (i.e., the auxin containing medium and the hormone-free medium) and are effective for this aspect of the invention. Examples of suitable media include combinations of MS salts, B5 salts or FNL salts with either MS vitamins or B5 vitamins. The somatic embryos thus induced are usually present as a cluster with more than 5 embryos of various sizes and are referred to herein as Type II Somatic Embryos (TIISEs). Continued culture of TIISEs on 2,4-D containing media lead to production of embryogenic calli. TIISEs and embryogenic calli are ideal for plant mass propagation and transformation.

The somatic embryos are then transferred to a medium for germination. Germination of somatic embryos can be improved with giberellic acid ($GA_3$) using a medium that is ½ or ¼ strength MS or B5 media. In one embodiment, the concentration of $GA_3$ is, for example from about 0.5 mg/l to about 10 mg/l, preferably from about 1 mg/l to about 5 mg/l and more preferably from about 2 mg/l to about 3 mg/l. The germinated embryos can be further developed in this medium for 2-6 weeks before transplanted to soil pots. The use of gelling agents, such as agar and phytagen, for preparing solid media is well known in the art. In one embodiment, the preferred gelling agent is phytagel. In this embodiment, the amount of phytagel is, for example, between about 2.2 g/l and 2.8 g/l.

In a third aspect of the present invention, an embryogenic liquid suspension culture is produced from the embryogenic calli or TIISEs produced in accordance with the second aspect of the invention. In one embodiment, the embryogenic calli or TIISEs are transferred to a liquid medium and subcultured regularly, usually every 2-3 weeks. Many known media can be used for the liquid medium and are effective for this aspect of the invention. Examples of suitable media include combinations of MS salts, B5 salts or FNL salts with either MS vitamins or B5 vitamins. In one embodiment the liquid medium is supplemented with one or more amino acids. In one embodiment, the amino acid is glutamine, asparagine or a combination of glutamine and asparagine. In one embodiment, the concentration of glutamine can be, for example, from about 0.1 g/l to about 2 g/l, preferably from about 0.2 g/l to about 1.5 g/l and more preferably from about 0.5 g/l to about 1.0 g/l. In one embodiment, the concentration of asparagine can be, for example, from about 0.1 g/l to about 2 g/l, preferably from about 0.25 g/l to about 1.0 g/l and more preferably from about 0.25 g/l to about 0.5 g/l. In one embodiment, the liquid medium contains an auxin. In one embodiment, an auxin that is effective in the liquid suspension culture system is 2,4-D in a concentration, for example from about 0.1 mg/l to about 0.5 mg/l, preferably from about 0.2 mg/l to about 0.3 mg/l. In one embodiment, the liquid medium has been modified to contain no $NH_4NO_3$ salts. Somatic embryos larger than 0.5 cm long are preferably removed by sieving during subcultures. The somatic embryos are matured and germinated as described herein. In one embodiment, the cultures are maintained in a shaking platform set at 60-100 rpm, preferably 70-90 rpm and more preferably 80 rpm. In one embodiment, the cultures are maintained at a temperature from about 20° C. to 35° C., and more preferably about 28° C. In one embodiment, the cultures are maintained with periods of light and dark, preferably with 16 hours of light. The liquid culture system is well suited for preparation a large batch of synchronized somatic embryos, which can be used for plant propagation and as explants for genetic transformation.

Under the above-mentioned conditions, a fraction of the somatic embryos may continue to mature to stages not suitable for initiation of new embryogenic calli in the liquid medium. These materials are excellent for re-initiation of embryogenic development paths if they are further matured in solid media designed to provide this re-initiation. In one embodiment, the material is first cultured on a solid medium that contains a high concentration of auxin followed by culturing on a solid medium that is hormone-free and that is further supplemented with amino acids. In one embodiment, an auxin that is effective is 2,4-D in a concentration, for example from about 0.1 mg/l to about 20 mg/l, preferably from about 1.0 mg/l to about 5 mg/l. In one embodiment, the amino acid is glutamine, asparagine or a combination of glutamine and asparagine. In one embodiment, the concentration of glutamine can be, for example, from about 0.2 g/l to about 2 g/l, preferably from about 0.2 g/l to about 1.5 g/l and more preferably from about 0.5 g/l to about 1.0 g/l. In one embodiment, the concentration of asparagines can be, for example, from about 0.2 g/l to about 1.5 g/l, preferably from about 0.2 g/l to about 1.0 g/l and more preferably from about 0.25 g/l to about 0.5 g/l. This embodiment is a practical supplement to the liquid suspension culture system providing large amount of explants for genetic transformation.

In a fourth aspect, the present invention provides a method of maintaining the liquid suspension culture so that the amount of callus tissue is increased and the germination of embryos is inhibited. In accordance with this aspect, somatic embryogenic callus tissue is maintained in suspension culture in a liquid maintenance medium and subcultured regularly, usually every 2-3 weeks. The liquid maintenance medium is a $NH_4NO_3$-free medium that contains MS salts and B5 vitamins. Other media such as B5 salts with B5 vitamins, or FNL salts with B5 vitamins could also be used. In one embodiment, the liquid maintenance medium is preferably supplemented with one or more amino acids. In one embodiment, the amino acid is glutamine, asparagine or a combination of glutamine and asparagine. In one embodiment, the concentration of glutamine can be, for example, from about 0.1 g/l to about 2 g/l, preferably from about 0.2 g/l to about 1.5 g/l and more preferably from about 0.5 g/l to about 1.0 g/l. In one embodiment, the concentration of asparagine can be, for example, from about 0.1 g/l to about 2 g/l, preferably from about 0.25 g/l to about 1.0 g/l and more preferably from about 0.25 g/l to about 0.5 g/l. In one embodiment, the liquid maintenance medium preferably contains an auxin. In one embodiment, an auxin that is effective in the liquid maintenance culture system is 2,4-D in a concentration, for example from about 0.1 mg/l to about 0.5 mg/l, preferably from about 0.2 mg/l to about 0.3 mg/l. In one embodiment, the liquid maintenance medium is further preferably supplemented with polyethylene glycol (PEG). In one embodiment, the amount of PEG in the medium can be, for example, from about 1% to about 15%, preferably from about 3% to about 10%, more preferably from about 3% to about 7%. In one embodiment, the PEG is suitable for plant tissue culture. In one embodiment, the average molecular weight of the PEG can be, for example, from about 1,000 to about 15,000, preferably from about 1,000 to about 10,000, more preferably from about 5,000 to about 10,000. Culturing in the liquid maintenance medium provides an increase in the mass of the callus tissue. This callus tissue is maintained more uniformly at globular stage or torpedo stage. The medium inhibits the germination of the embryos.

The present invention can be practiced using a plant that is a member of the genera *Jatropha*, preferably, *Jatropha curcas* or an artificial hybrid of *Jatropha curcas* that contains a substantial amount of the genomic DNA of *Jatropha curcas*. Example of such artificial hybrids are F1 of *J. curcas*×*J. intergerima* and its backcrossed offspring (Sujatha and Prabakaran, 2003). The present invention provides complete and efficient systems which can be used for regeneration of plants in the genera of *Jatropha*. Numerous somatic embryos have been produced by these systems and the regenerants have been demonstrated to be completely normal in vegetative development and sexual reproduction, i.e., sexually fertile plants are obtained.

In addition, the present invention provides systems which can be used for the transformation of plants of the genera *Jatropha*. The method of transformation/transfection is not critical to the transformation of plants of the genera *Jatropha*; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed. See, for example, Mathews et al. (1992), Neuhaus et al. (1987), Wilde et al. (1992), U.S. Pat. Nos. 7,241,937, 7,273,966 and 7,291,765 and U.S. Patent Application Publication Nos. 2007/0231905 and 2008/0010704. See also, International Published Application No. WO2005/103271.

In one embodiment, the explant tissue can be co-cultured with an *Agrobacterium* strain harboring a DNA construct containing a gene or nucleic acid of interest using techniques well known in the art. Transformed tissue can be selected using conventional techniques well known in the art. In another embodiment, the embryogenic liquid suspension cultures can be co-cultured with an *Agrobacterium* strain harboring a DNA construct containing a gene or nucleic acid of interest using techniques well known in the art. Transformed tissue can be selected using conventional techniques well known in the art. In a further embodiment, the DNA can be introduced into the explant tissue or cells of the embryogenic liquid suspension culture using conventional techniques, such as particle bombardment. Transformed tissue can be selected using conventional techniques well known in the art. Transformed or transgenic plants can be regenerated using the methods described herein.

Similarly, the DNA that is inserted (the DNA of interest) into plants of the genera *Jatropha* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley—VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Media

5K MS salts, B5 vitamins, 30 g/l sucrose, 2.2 g/l phytagel, 5 mg/l 2,4-D, 0.1 mg/l kinetin, pH 5.8

10K MS salts, B5 vitamins, 30 g/l sucrose, 2.2 g/l phytagel, 10 mg/l 2,4-D, 0.1 mg/l kinetin, pH 5.8 d20 MS salts, B5 vitamins, 30 g/l sucrose, 2.2 g/l phytagel, 2,4-D 20 mg/l 2,4-D, pH 5.8

EGA0 $NH_4NO_3$-deficient MS salts, B5 vitamins, 30 g/l glucose, 2.4 g/l phytagel, 1 g/l glutamine, 0.5 g/l asparagines)

EGAh $NH_4NO_3$-deficient MS salts B5 vitamins, 30 g/l sucrose, 2.4 g/l phytagel, 1 g/l glutamine, 0.5 g/l asparagine, 0.95 g/l $KNO_3$)

DGA $NH_4NO_3$-free MS salts, B5 vitamins, 30 g/l sucrose, 2.2 g/l phytogel, 1 g/l glutamine, 0.5 g/l asparagine, pH 5.8.

G13 MS salts, B5 vitamins, 3 mg/l $GA_3$, 30 g/l sucrose, 2.2 g/l phytagel, pH 5.8.

G12-1 1/2MS salts, 1/2B5 vitamins, 0.01 mg/l naphthaleneacetic acid (NAA), 200 mg/l casein hydrolysate, 15 g/l sucrose, 3 g/l phytagel, pH 5.8.

See Murashige and Skoog (1962) for a general description of the MS media components and Gamborg et al. (1968) for a general description of the B5 media components.

Example 2

Tissue Culture Conditions and Preparation of Aseptic Explants

Unless stated otherwise, plant materials were cultured in 90 mm Petri dishes which were placed on lighted shelves in a clean room with 16-8 hours day-night cycles and 28° C. constant temperature. Lighting was provided by 1-4 Phillips Fluotone tubes (36 W) with about 60-150 μmol/m²/s photosynthetic photon flux (PPF).

Seedlings were harvested on the 5th-7th days after sowing into the soil. Surface-sterilization was done by washing in 10% $H_2O_2$ for 20 minutes followed by rinsing with sterilized water for three times. Developing fruits were sterilized by soaking in 70% ethanol for 30 minutes followed by washing in sterilized water three times. Developing seeds and zygotic embryos were dissected with surgical scalper blades under a stereomicroscope placed inside a laminar flow.

Liquid cultures were performed in 65 mm plastic cylinder containers or 250 ml glass conical flasks that were placed in shakers set at 80 rpm, 28° C. constant temperature and 16-8 hours day-light cycles.

Example 3

Effect of Explants on Induction of Somatic Embryogenesis

We surveyed the effect of various explants and hormone concentrations on induction of somatic embryos in *Jatropha curcas*. Seedlings harvested 5-7 days after sowing into the soil were surface-sterilized and stem, leave, petiole, cotyledon, hypocotyls from the germinated seeds were excised and cut into approximately 0.5 cm in length. The explants were cultured on numerous solid media containing MS salts and B5 vitamins supplemented with 0-20 mg/l 2,4-D, 0-0.01 mg/l naphthaleneacetic acid (NAA) and 0-1 mg/l cytokinins, for example, kinetin, 6-benzylaminopurine (BAP), N6-(2-isopentenyl)adenine (2ip), zeatin or zeatin riboside. The explants and calli were subcultured about every two weeks in the same medium or in a hormone-free medium. Modified $NH_4SO_4$-free media with double concentration of $KNO_3$ (1.9 g/l) were also used in the subculture. No somatic embryos were observed after at least four months in all the media tested.

Example 4

Effects of 2,4-D on Somatic Embryogenesis from Zygotic Embryo Explants

Developing fruits were surfaced sterilized. The immature zygotic embryos and endosperms (En) were separated from each other using a surgical scalper blade. Zygotic embryos longer than 0.5 cm were further cut at the cotyledon-hypocotyl junction to produce explants of cotyledons only and hypocotyls with the root radicals. Zygotic embryos shorter than 0.5 cm were cultured intact as they are too fragile. We classified these explants as cotyledons (Cot); hypocotyls with root radicals (Rh); intact embryos (Eb) and endosperm (En).

The explants were cultured on a solid medium comprising MS salt, B5 vitamins and various concentrations of 2,4-D ranging from 0.1 to 20 mg/L. Kinetin was added at 0.1 mg/L in some of the treatments. Somatic embryos started to emerge without obvious sign of calli formation around $10^{th}$ day, which predominantly formed on the edge of the endosperm tissues where the embryo had been detached. The somatic embryos most likely originated from the residual diploid cells of the zygotic embryo tissue attached on the endosperm. The preference to form somatic embryos at the endosperm-zygotic embryo junction suggests the endosperm tissue might be providing extra signal or nutrients that were necessary for the initiation and development of somatic embryos. These somatic embryos developed speedily and predominantly matured as single embryo (FIG. 1). We called them Type I Somatic Embryo (TISE). TISEs were observed in all media tested although 2,4-D appeared to be inhibitory at high levels (Table 1).

TABLE 1

Effects of 2,4-D and Medium Shifting on Formation of Somatic Embryos

| 2,4-D (mg/L) | Total Explants | TISE Count* | TISE (%) | TIISE Count** | TIISE (%) |
|---|---|---|---|---|---|
| 0.1 | 19 | 16 | 84 | 2 | 11 |
| 0.2 | 28 | 15 | 54 | 1 | 4 |
| 0.5 | 16 | 8 | 50 | 3 | 19 |
| 1 | 19 | 8 | 42 | 0 | 0 |
| 2 | 25 | 19 | 76 | 9 | 36 |
| 5 | 23 | 13 | 57 | 9 | 39 |
| 10 | 21 | 9 | 43 | 5 | 24 |
| 20 | 13 | 5 | 38 | 3 | 23 |

*Explants and calli were cultured for 8 weeks in media comprised of MS salts, B5 vitamins, 0.1 mg/l kinetin and the amount of sodium 2,4-dichlorophenoxyacetic acid indicated.
**TIISEs were observed after shifting calli that had been cultured in the respective medium for 4 weeks to DGA medium. The formation of TIISEs was investigated at the end of the 6th week culture in DGA medium. The result was compiled from several separate experiments. The zygotic embryos used were in a range between 0.2 cm and 1.7 cm in length at the time of collection.

Figure 2:
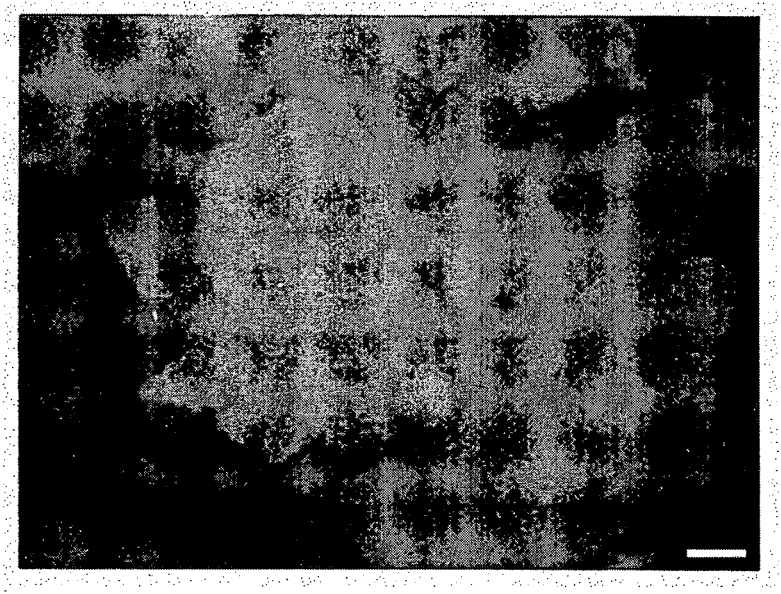
FIG. 2 shows Type II somatic embryo (TIISE) formation. Hypocotyl explants were induced to form TIISE, which was differentiated in DGA medium, germinated in G13 medium. Scale bar represents 1 mm.
Figure 3A:
FIGS. 3A-3E show stages in plant regeneration.
Figure 3B:
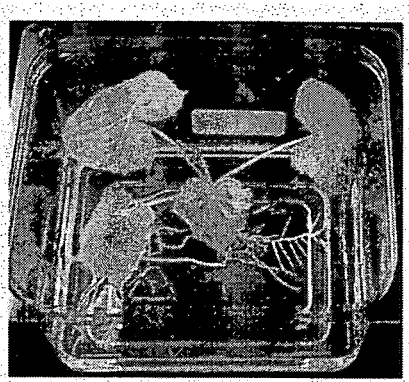
Figure 3C:
Figure 3D:
Figure 3E:

Yellowish or white calli were observed on the explants from 3rd week if subcultured in the same medium. Extensively tested variables for induction of somatic embryogenesis were media of numerous compositions. Combinations of MS salt, Gamborg B5 salts, MS vitamins, Gamborg B5 vitamins; presence or absence of NH4NO3; amount of KNO3 (1.9-3.8 g/l); organic nitrogen source, e.g., free amino acids, casein hydrolysate; trace amount of hormones, e.g., kinetin (0-1 mg/l), benzyl adenine (0-1 mg/l); choice of carbon sources, e.g., glucose, sucrose and maltose; and activated carbon (5 g/l). In a large number of media, the calli died within 1-2 weeks when shifted into a new medium. In contrast, somatic embryos were observed in some calli which had been transferred to a hormone-free MS medium with B5 vitamins, glutamine and asparagines. An example of the medium is DGA medium in which 1 g/l glutamine and 0.5 g/l asparagines was supplemented. A cluster of somatic embryos of various stages emerged around the 10th day after the medium shift to DGA (FIG. 2). EGAD or EGAh were also effective in induction of somatic embryogenesis although calli growth was less healthy. Close examination of the DGA, EGAD and EGAh revealed that all three media contained glutamine and asparagine, demonstrating the vital role of organic nitrogen source, such as amino acids.

Somatic embryos formed in DGA medium underwent multiplication and maturation simultaneously. We called them Type II Somatic Embryos (TIISE). TIISEs were preferentially formed on explants previously cultured in media containing higher concentration of 2,4-D, for example, 2-5 mg/l during the first induction culture (Table 1).

Example 5

Effect of 2,4-D Concentration and Zygotic Embryo Size

Developing fruits were surfaced-sterilized and dissected to yield 200 immature zygotic embryos that were shorter than 1.5 cm in length. The embryos were separated into two groups, "<0.5 cm" and "0.5-1.5 cm". The endosperm and zygotic embryo explants were cultured on solid media with various concentration of 2,4-D. On the 5th day, the embryos, which became greenish, enlarged and hardened, were removed from the endosperms and cut into small pieces of about 0.25 cm$^2$ each. The endosperm and embryo explants were cultured separately on the same media in the dark at 28° C. It was confirmed that most somatic embryos were produced on the endosperm explants where the embryos had been detached. Table 2 summarizes the results of somatic embryos and calli formation at the end of the 3rd week. It is apparent that, although 2,4-D was not essential for initiation of somatic embryos; low concentration of it causes excessive expansion of explants. Calli formation appeared more favorable at about 0.5-10 mg/l 2,4-D. The size of zygotic embryos in the range tested did not appear to affect significantly induction of somatic embryogenesis.

TABLE 2

Effects of 2,4-D Concentration and Zygotic Embryo Developmental Stage

| 2,4-D (mg/L) | SE Count (ZE < 0.5 cm) | | SE Count (ZE 0.5-1.5 cm) | | SE Count (Overall) | Explant Development | | |
|---|---|---|---|---|---|---|---|---|
| | ZE | En | ZE | En | SE (%) | Root Length | Hypocotyl Length | Calli Size |
| 0 | 1 | 6 | 0 | 0 | 35 | +++++ | +++++ | + |
| 0.1 | 0 | 5 | 0 | 6 | 55 | ++++ | +++++ | ++ |
| 0.2 | 0 | 7 | 0 | 2 | 45 | +++ | ++++ | ++ |
| 0.5 | 0 | 5 | 0 | 6 | 55 | ++ | +++ | +++ |
| 1 | 0 | 7 | 1 | 3 | 55 | ++ | +++ | ++++ |
| 2 | 0 | 3 | 0 | 5 | 40 | + | + | ++++ |
| 5 | 0 | 2 | 0 | 1 | 15 | + | + | +++ |
| 10 | 0 | 3 | 0 | 0 | 15 | + | + | +++ |
| 15 | 0 | 1 | 0 | 0 | 5 | + | + | ++ |
| 20 | 0 | 0 | 0 | 0 | 0 | + | + | + |

1. The basal medium was MS salt with B5 vitamins, 0.1 mg/L kinetin, 30 g/l sucrose, 2.2 g/l phytagel, pH 5.8.
2. Twenty explants were used in each treatment.
3. The relative size of explants and calli are indicated by the number of + symbols.
4. ZE: zygotic embryo; SE: somatic embryo

Example 6

Effect of Kinetin

Developing fruits were surface-sterilized and dissected to yield 120 immature embryos that were shorter than 1.5 cm in length. After cutting into halves, the explants were cultured in media with a series of kinetin concentrations. On the 5th day, the endosperm tissues were separated from the embryos, further reduced into small pieces of about 0.25 cm$^2$ and transferred to the fresh medium with the same kinetin concentrations. After one subcultures (6 weeks in total), the calli were transferred to DGA medium and cultured for one month. Twenty immature embryos were used in each treatment. It was observed that TISEs were almost exclusively formed on endosperm tissues where the embryos had been detached after three's culture. Table 3 shows the explants that had produced embryos or embryogenic calli after shifting to DGA medium for 4 weeks. The results indicate that kinetin played little role in induction of TISEs. In fact, it appeared to negatively affect TIISEs formation under the conditions tested.

TABLE 3

Effect of Kinetin

| Kinetin (mg/l) | TISE (%) | TIISE (%) | | |
|---|---|---|---|---|
| | | Total | >5 SE | >10 SE |
| 0 | 25 | 40 | 20 | 5 |
| 0.05 | 35 | 25 | 15 | 0 |
| 0.1 | 35 | 30 | 15 | 5 |
| 0.2 | 40 | 30 | 15 | 0 |
| 0.5 | 25 | 20 | 10 | 5 |
| 1 | 45 | 15 | 0 | 0 |

The basic medium was MS salts, B5 vitamins, 5 mg/l 2,4-D, 30 g/l sucrose, 2.2 g/l phytagel, pH 5.8. twenty En and Eb explants were used in each treatment.

Example 7

Effect of Embryo Developmental Stages

Immature zygotic embryos together with the endosperm tissues were prepared as previously described and were cultured in medium 10K for 5 days. The pre-cultured explants were separated at the endosperm-embryo junctions, sorted out according to the length of embryos into four groups, i.e., <0.5 cm, 0.5-1.0 cm, 1.0-1.5 cm and >1.5 cm. The embryos and endosperm tissues from twenty developing seeds in each group were cultured in medium 10K. Three weeks later, they were subcultured in medium 5K for another three weeks to induce formation of calli, which were transferred to DGA to induce somatic embryogenesis. The calli were subculured two weeks later in the same medium. Table 4 summarizes the formation of TISEs and TIISEs 22 days after shifting to DGA medium. It is obvious that developing seeds with its zygotic embryos longer than 1.5 cm are not suitable for induction of somatic embryogenesis. Importantly, production of both TISEs and TIISEs were more favorable in zygotic embryos shorter than 1.5 cm.

TABLE 4

Effect of Developmental Stages of Immature Zygotic Embryo on Induction of Somatic Embryogenesis.

| | | TIISE | | |
|---|---|---|---|---|
| ZE Size | TISE % | Total (%) | >5 SE (%) | >10 SE (%) |
| <0.5 cm | 2.5 | 20 | 2.5 | 0 |
| 0.5-1 cm | 5 | 17.5 | 5 | 5 |
| 1-1.5 cm | 7.5 | 25 | 12.5 | 2.5 |
| >1.5 cm | 0 | 7.5 | 0 | 0 |

ZE: zygotic embryo; SE: somatic embryo; >5 SE (%): percent of calli with more than 5 somatic embryos from a single origin; >10 SE %: percent of calli with more than 10 somatic embryos from a single origin.

Example 8

Effect of Tissue Organ Type on Induction of Somatic Embryogenesis

The origins of 60 TIISEs were traced from experiments in Examples 6 and 7. All TIISEs examined were derived from calli after being shifted to DGA medium for 31 days. The results are summarized in Table 5. As we suspect that the TISE derived from endosperm tissue may actually from the residual hypocotyl cells, the hypocotyl-root apex is a much preferred tissue for induction of somatic embryogenesis in *Jatropha curcas*.

TABLE 5

Effects of Tissue Organ Type on Somatic Embryogenesis

| Organ | TIISE Calli Count | TIISE Calli (%) |
|---|---|---|
| Cotyledon | 10 | 16.7 |
| Hypocotyl/root | 30 | 50 |
| Endosperm | 20 | 33.3 |

TIISEs from endosperm tissues were derived from secondary embryos of TISEs.

Example 9

Effect of Light

Immature zygotic embryos (0.5-1.5 cm long) were cultured in "d20" medium for five days. The embryos were separated from the endosperm tissue; cultured in "10K" medium for three weeks; and subcultured in medium "5K" for another 3 weeks before shifted to DGA medium. Twenty embryos and 20 endosperm explants were cultured under either total darkness or under weak lighting (about 60 μmol/m$^2$/s) cycles (16 hours light per day). Table 6 summarizes the formation of TISEs and TIISEs that were derived from the original explants or calli recorded 38 days after culturing in DGA medium. It showed that lighting does not affect a major role in induction of TIISE.

TABLE 6

Effect of Light

| | | TIISE | | |
|---|---|---|---|---|
| Treatment | TISE (%) | Total (%) | >5 SE (%) | >10 SE (%) |
| Light | 20 | 15 | 5 | 0 |
| Dark | 5 | 20 | 5 | 5 |

Example 10

Effect of Basal Medium Composition

Twenty immature zygotic embryos were pre-cultured for 5 days and cultured for 29 days in various basal media with 5 mg/l 2,4-D, 30 g/l sucrose and 2.2 g/l phytagel. After 6 weeks induction in the DGA medium, the formation of TIISE is shown in Table 7, which clearly demonstrates the Gamborg B5 salts with B5 vitamins is the preferred medium for induction of TIISEs although all media worked satisfactorily.

TABLE 7

Effect of Basal Salts and Vitamins

| | | TIISE | | |
|---|---|---|---|---|
| medium | TISE (%) | Total (%) | SE >5 (%) | SE >10 (%) |
| MS salt, B5 vitamins | 30 | 15 | 5 | 5 |
| MS salts, MS vitamins | 40 | 25 | 15 | 10 |
| B5 salts, B5 vitamins | 15 | 50 | 25 | 15 |
| NH$_4$NO$_3$-free-MS salts, B5 vitamins | 40 | 25 | 10 | 5 |
| FNL salts, B5 vitamins | 50 | 25 | 10 | 0 |

Composition of FNL salts can be found in Samoylov et al., (1998).

Example 11

Maturation and Germination of Somatic Embryos

Somatic embryos were able to progress into near maturity in DGA medium and the cotyledonary stage somatic embryos were able to germinate into a complete plantlet in same media although the efficiency tended to be low. We found that supplementation of maltose and reduction of sucrose concentration significantly improved embryo maturation as evidenced by the higher conversion rates to plantlets (Table 8). We further found that secondary embryos were abundantly produced, mostly at the root of mature embryos.

TABLE 8

Media for Maturation of Somatic Embryos

| Carbon Source | Viable Plantlet Count | Viable Plantlets (%) |
|---|---|---|
| 30 g/l sucrose | 9 | 7.50 |
| 20 g/l sucrose 20 g/l maltose | 15 | 12.50 |
| 10 sucrose 40 g/l maltose | 10 | 8.33 |
| 60 g/l maltose | 14 | 11.67 |

1. 120 somatic embryos that were between 0.5-1 cm long were cultured in the respective medium for one month and then transferred to G13 medium for another month. Plantlets were observed after further cultured in G12-1 medium for one month.
2. Salt medium is NH$_4$NO$_3$-free MS salt, B5 vitamins, 1 g/l glutamine, 0.5 g/l asparagine, 2.2 g/l phytagel, pH 5.8.

In addition, we tested the effect of casein hydrolysate on embryo maturation and germination. Casein hydrolysate between 0-400 mg/l were supplemented in media with NH$_4$NO$_3$-free MS salts, B5 vitamins, 1 g/l glutamine, 0.5 g/l asparagine, 20 g/l Sucrose, 20 g/l maltose, 2.2 g/l phytagel, pH 5.8. Casein hydrolysate had apparent promoting effect on the maturation of somatic embryos (Table 9).

TABLE 9

Effect on Casein Hydrolysate on Maturation and Germination

| Casein hydrolysate (mg/L) | Germination Rate (%) |
|---|---|
| 0 | 6.25 |
| 100 | 17.50 |
| 300 | 15.00 |
| 400 | 12.50 |

1. 80 somatic embryos were used in each treatment.
2. Matured somatic embryos were germinated in G13 for one month.

To further explore methods to improve germination, abscisic acid (ABA) between 0-5 mg/l was supplemented in DGA or EGA media or their variants with 10-30 g/l sucrose and 20-60 g/l maltose. Improvement of germination in MS medium was not observed and in most cases and plantlet abnormality was apparently increased. On the other hand, gibberellic acid ($GA_3$), which is well known to acts as a key signaling molecule during germination of natural seeds (Takahashi et al, 1991), significantly improved germination in many media tested. Examples of the effects are shown in Table 10, where 20-30 TISEs were transferred to various media listed below. Except in ¼ strength MS medium, few somatic embryos germinated without $GA_3$. In MS and ½ MS media, supplementation of 2-3 mg/l $GA_3$ significantly improved development of viable plantlets (Viable Germination) with 2 mg/l $GA_3$ appeared to be optimal. Reducing the strength of basal salts was likewise beneficial to germination of somatic embryos. Addition of B5 vitamins did not significantly affect germination (data not shown).

TABLE 10

Effect on $GA_3$ on Germination of Somatic Embryos

| Medium | $GA_3$ (mg/L) | Explant Counts | Root Growth SE Count | % | Hypocotyl Extension SE Count | % | Viable Germination SE Count | SE % |
|---|---|---|---|---|---|---|---|---|
| Full | 0 | 20 | 6 | 30 | 4 | 13 | 0 | 0 |
|  | 2 | 30 | 16 | 53 | 16 | 30 | 9 | 30 |
|  | 3 | 30 | 11 | 37 | 16 | 44 | 2 | 5 |
| ½ Strength | 0 | 20 | 4 | 20 | 5 | 25 | 0 | 0 |
|  | 2 | 30 | 8 | 27 | 9 | 34 | 7 | 21 |
|  | 3 | 30 | 16 | 53 | 14 | 26 | 6 | 23 |
| ¼ Strength | 0 | 20 | 3 | 15 | 3 | 20 | 2 | 10 |
|  | 2 | 30 | 13 | 43 | 14 | 32 | 6 | 19 |
|  | 3 | 30 | 14 | 47 | 12 | 26 | 2 | 8 |

1. MS salt and B5 vitamins were used at different strength while carbon source was kept constant at 30 g/l sucrose.
2. 2.8 g/l phytagel was used as solidifying agent.
3. Results were recorded after subjecting the somatic embryos in the media for three weeks.

Example 12

Whole Plant Development

More than 30 plantlets originated from TISE or TIISE have been acclimatized and potted to soil in pots. To date, eight plants have set seeds and no obvious abnormality was seen in any of the plants. The plantlets flowered in less than four months after potting and produced normal fruits and seeds (FIG. 3.)

Example 13

Re-Initiation of Somatic Embryogenesis of Matured Somatic Embryos

Figure 4A:
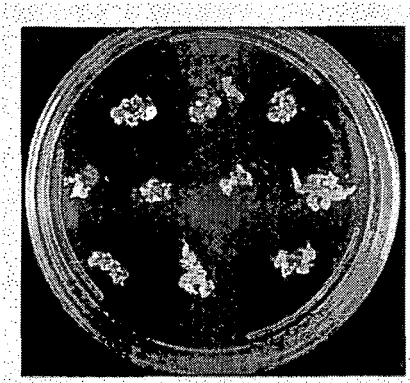
FIGS. 4A-4D show the effects of glutamine, asparagine and $KNO_3$. Somatic embryos were exposed to modified DGA media and photographed 4 weeks later.
Figure 4B:
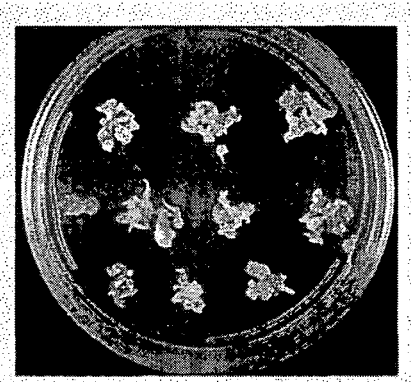
Figure 4C:
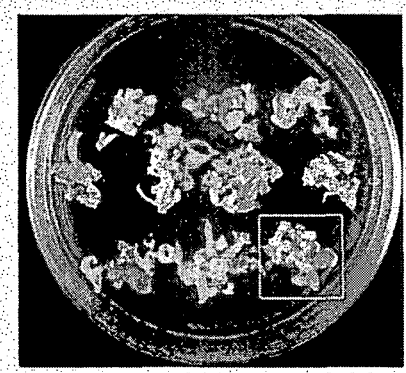
Figure 4D:

Somatic embryos were matured in 2,4-D-free liquid MS medium and hypocotyl-root apex tissues were excised from somatic embryos larger than 0.5 cm. Those smaller than 0.5 cm were cultured intact. The explants were cultured in various DGA or its derivative solid medium. Similar to zygotic embryos explants, glutamine and asparagine supplementation greatly improved production of secondary somatic embryos and embryogenenic calli (compare FIGS. 4A and 4B). Increase in KNO3 favored embryo differentiation but inhibited maturation (compare FIGS. 4B and 4C). Somatic embryos of all size ranges tested could be efficiently induced to form secondary embryos and embryogenic calli in the solid media and (Table 11). 2,4-D and kinetin could be added as optional supplements (not shown).

TABLE 11

Somatic Embryos as Explants for Induction of Somatic Embryogenesis

| Explant | SE Size | medium | TIISES SE Count | SE (%) |
|---|---|---|---|---|
| Hypocotyl-Root apex | >1 cm | DGA | 14 | 47 |
|  |  | DGAGA | 13 | 43 |
|  |  | DGAGAh | 13 | 43 |
|  |  | DGAGAhh | 15 | 50 |
|  |  | DGAh | 12 | 40 |
|  |  | DGAhh | 16 | 53 |

TABLE 11-continued

Somatic Embryos as Explants for Induction of Somatic Embryogenesis

| Explant | SE Size | medium | TIISES SE Count | SE (%) |
|---|---|---|---|---|
| Whole Embryos | 0.5-1.0 cm | DGA | 19 | 63 |
|  |  | DGAGA | 10 | 33 |
|  |  | DGAGAh | 10 | 33 |
|  |  | DGAGAhh | 20 | 67 |

TABLE 11-continued

Somatic Embryos as Explants for Induction
of Somatic Embryogenesis

| Explant | SE Size | medium | TIISES SE Count | SE (%) |
|---|---|---|---|---|
| | | DGAh | 8 | 27 |
| | | DGAhh | 6 | 20 |
| Whole | <0.5 cm | DGA | 19 | 95 |
| Embryos | | DGA + GA | 15 | 75 |
| | | DGA + GAn | 13 | 65 |
| | | DGA + GAN | 6 | 30 |
| | | DGA + n | 13 | 65 |
| | | DGA + N | 12 | 60 |

1. 30 explants were used in each treatment.
2. All media were solidified with 2.2 g/l phytagel.
3. +GA: doubled the amount of glutamine and asparagine to 2 g/l and 1 g/l, repectively; +GAn: As + GA, plus 0.95 g/l $KNO_3$; +GAN: as +GA plus 1.9 g/l $KNO_3$; +n: plus 0.95 g/l $KNO_3$; +N: plus 1.9 g/l $KNO_3$.

Example 14

Preparation of Embryogenic Liquid Suspension Cultures

Figure 5A:
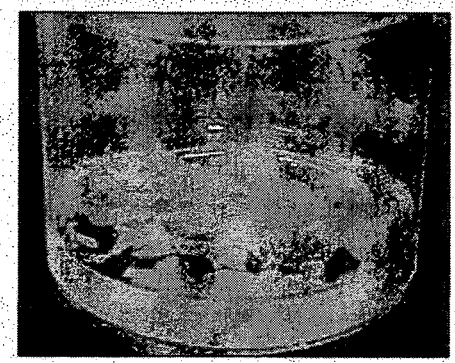
FIGS. 5A-5D show embryogenic liquid suspension culture. About 50 mg embryogenic calli produced in solid DGA medium were inoculated in 20 ml modified DGA liquid media. Embryos larger than 2 mm were removed before inoculation. Subculture was done every two weeks. Photos were taken after 2 subcultures.
Figure 5B:
Figure 5C:
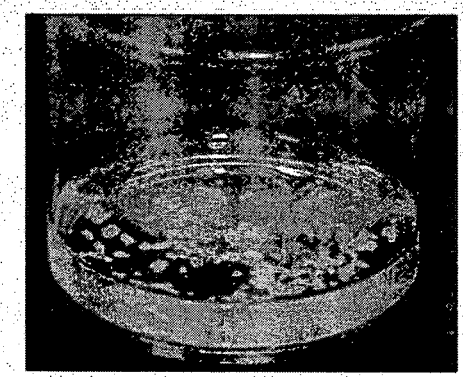
Figure 5D:
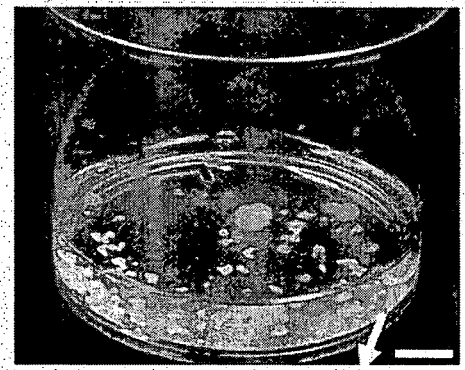

Effects 2,4-D and carbon source on establishment of somatic embryogenic liquid suspension culture was investigated. While solid DGA medium supported efficient production of secondary embryos and embryogenic calli, it failed to do so in liquid medium. At sucrose level ranging from 10-30 g/l, continued culture lead to maturation of the somatic embryo with no new initiation of secondary embryos (FIG. 5A). The somatic embryos thus produced share good synchrony and are excellent materials for re-induction of TIISEs (Refer to Example 13). When 2,4-D was higher than 0.5 g/l, calli multiplication and embryogenicity was poor resulting in production of large ball-shaped calli (FIG. 5D, indicated by the arrow) which failed to re-initiate somatic embryogenesis even when transferred back to solid DGA medium. Supplementation of low concentration of 2,4-D, for example, 0.1-0.5 g/l, significantly inhibited maturation of somatic embryos and allowed re-initiation of secondary embryoids production (FIG. 5B). Increasing KNO3 to 1.9 g/l to 3.8 g/l facilitated maintaining the liquid suspension culture at early stages of embryogenesis. The suspension cultures were stable for months if large embryos were removed. Further, sucrose concentration needs to be reduced below about 20 g/l (compare FIGS. 5B and 5C).

Example 15

Duration of Calli Initiation on Induction of TIISEs

Immature zygotic embryos were excised, separated from endosperm tissue and induced between 2-6 weeks in a solid medium with $NH_4NO_3$-free B5 salts, B5 vitamins, 5 mg/l 2,4-D, 30 g/l sucrose, 2.2 g/l phytagel, pH 5.8. The explants were subcultured every two weeks before shifted to the solid DGA medium for two months. The results are shown in Table 12. A two week's induction is apparent sufficient. However, to maximize production of TIISEs with more than 5 somatic embryos in each location, extend induction duration to 4 weeks produced markedly improved result.

TABLE 12

Duration of Calli Initiation on Somatic Embryo Induction

| Induction Duration | TISE (%) | TIISE (%) Overall (%) | >5 SE (%) | >10 SE (%) |
|---|---|---|---|---|
| 2 weeks | 10 | 50 | 20 | 0 |
| 4 weeks | 15 | 45 | 40 | 15 |
| 6 weeks | 5 | 45 | 15 | 5 |

20 immature zygotic embryos were used in each treatment.

Example 16

Effect of PEG on Maintenance of Embryogenic Liquid Suspension Culture

Figure 6:
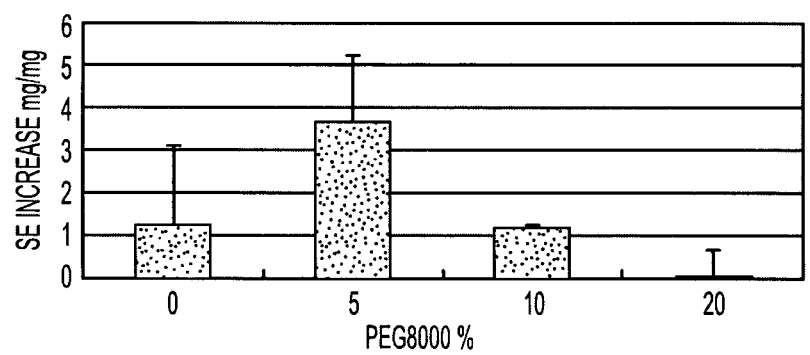
FIG. 6 shows the effect of PEG on maintenance of liquid suspension culture. Somatic embryogenic calli was maintained in $NH_4NO_3$-free MS medium, B5 vitamins, 20 g/l sucrose, 1.9 g/l $KNO_3$ (total), 0.5 g/l glutamine, 0.25 g/l asparagine, 0.3 mg/l 2,4-D. About 200 mg calli was taken out and cultured with the sample medium or supplemented with 5%, 10% and 20% PEG8000, respectively. The cultures were subcultured every two weeks. At the $8^{th}$ week, total calli mass was determined. The net increases in calli mass are shown. The average of three independent experiments are shown.

Somatic embryogenic calli was maintained in $NH_4NO_3$-free MS medium, B5 vitamins, 20 g/l sucrose, 1.9 g/l $KNO_3$ (total), 0.5 g/l glutamine, 0.25 g/l asparagine, 0.3 mg/1 2,4-D. About 200 mg calli was taken out and cultured with the sample medium or supplemented with 5%, 10% and 20% PEG8000, respectively. The cultures were subcultured every two weeks. At the $8^{th}$ week, total calli mass was determined. The net increases in calli mass are shown in FIG. 6. From the average of three repeats, it was clear that supplementation of 5% PEG8000 lead to about three fold increase in calli mass. Importantly, the calli thus cultured was maintained more uniformly at globular stage or torpedo stage and totally inhibited embryo germination.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Armstrong, T. I. and Deboer, D. L. (2000). Method for the regeneration of cotton. WO 2000/036911.

Becwar, M. R. et al. (1995). Method for regeneration of coniferous plants by somatic embryogenesis. U.S. Pat. No. 5,413,930.

Becwar, M. R. et al. (1996). Method for regeneration of coniferous plants by somatic embryogenesis. U.S. Pat. No. 5,506,136.

Buffard-Morel, J. et al. (1994). Process for regenerating the coconut palm from explants, and plants obtained by such process. WO 1994/016551.

Cai, L. and Ji, L. (2005). Methods for high efficiency transformation and regeneration of plant suspension cultures. WO/2005/103271

Chee, P, P. (1991). Somatic embryogenesis of squash. WO 1991/004332.

Chee, P. P. (1997). Somatic embryogenesis and transformation of squash. U.S. Pat. No. 5,677,157.

Christensen, A. H. and Quail, P. H, (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

Collins, G. B. et al. (1991). Transformation, somatic embryogenesis and whole plant regeneration method for Glycine species. U.S. Pat. No. 5,024,944.

Conrad, R. S. (1996). Method for applying hydrogel coatings to embryonic plants. U.S. Pat. No. 5,572,827.

Cooley, G. L. and Wilcox; A. S. (1987). Sunflower regeneration through embryogenesis. U.S. Pat. No. 4,670,392.

Côte, F. X. et al. (2000). Field performance of embryogenic cell suspension-derived banana plants (Musa AAA, cv. Grande naine). *Euphytica* 112:245-251.

Dodeman, V. L. et al. (1997). Zygotic embryogenesis versus somatic embryogenesis. *J Exp Bot* 48:1493-1509.

Eudes, F. A. G. et al. (2006). Process for inducing direct somatic embryogenesis in immature scutella cells of pooideae, and rapidly regenerating fertile plants. U.S. Pat. No. 6,995,016.

Fki, L. et al. (2003). An optimised protocol for plant regeneration from embryogenic suspension cultures of date palm, *Phoenix* dactylifera L., cv. Deglet Nour. *Plant Cell Rep* 21:517-524.

Gamborg, O. L. et al. (1968). Nutrient requirements of suspension cultures of soybean root cells. *Exp Cell Res* 50:151-158.

Garay, R. et al. (2003). Regenration of agave tequilana weber var. *Azul* plants using indirect somatic embryogenesis. WO 2003/039244.

Genovesi, A. D., Yingling, R. A. (1995). Isolated microscope and anther culture of maize. U.S. Pat. No. 5,445,961

Guiltinan, M. J. et al. (2001). Methods and tissue culture media for inducing somatic embryogenesis, *agrobacterium*-medicated transformation and efficient regeneration of cacao plants. U.S. Pat. No. 6,197,587.

Handley III, L. W. (1998). Method for regeneration of coniferous plants by somatic embryogenesis. U.S. Pat. No. 5,731,203.

Jha, T. B. et al, (2007). Somatic embryogenesis in *Jatropha curcas* Linn., an important biofuel plant. *Plant Biotechnology Reports* 1:135-140.

Jouenne, M. O. et al. (1995). Method for encouraging secondary somatic embyogenesis and application to the regeneration of plants, in particular the grape. WO 1995/008262.

Kasha, K. and Simion, E. (2001). Embryogenesis and plant regeneration of from microspores. WO 2001/041557.

Kasha; K. J. and Simion, E. (2004). Embryogenesis and plant regeneration from microspores. U.S. Pat. No. 6,812,028.

Last, D. I. et al. (1991). pEmu: an improved promoter for gene expression in cereal cells. *Theor Appl Genet.* 81:581-588.

Mathews, H. et al. (1992). Stable integration and expression of beta-glucuronidase and NPT-II genes in mango somatic embryos. *In Vitro Cell Develop Biol—Plant* 28P:172-178.

McElroy, D. et al. (1990). Isolation of an efficient actin promoter for use in rice transformation. *Plant Cell* 2:163-171.

Merkle, S. A. and Dean, J. F. (2000). Forest tree biotechnology. *Cur Opin Biotechnol* 11:298-302.

Murashige, T. and Skoog, F. (1962). A revised medium for rapid growth and bioassays with tobacco tissue cultures. *Physiol Plant* 15:473-497.

Neuhaus, G. et al. (1987). Transgenic rapeseed plants obtained by microinjected DNA into microspore-derived embryoids. *Theor Appl Genet.* 75:30-36.

Odell, J. T. et al. (1985). Identification of DNA sequences required for activity of the cauliflower mosaic virus 35S promoter. *Nature* 313:810-812.

Rutter, M. R. et al. (1998a). Method for regeneration of coniferous plants by somatic embryogenesis employing polyethylene glycol. U.S. Pat. No. 5,731,191.

Rutter, M. R. et al. (1998b). Method for regeneration of coniferous plants by somatic embryogenesis employing polyethylene glycol. U.S. Pat. No. 5,731,204.

Samoylov, V. et al. (1998). A liquid-medium-based protocol for rapid regeneration from embryogenic soya bean cultures. *Plant Cell Rep* 18:49-54.

Seabrook, J. E. A. et al. (1999). Regeneration of somatic embryos from plant tissues. WO 1999/038373, Schoofs, H. M. E. et al. (1998). Method for generating embryogenic cell culturs for the production of bananas (*Musa* spp). WO 1998/036636.

Sondahl, M. R. et al. (1993). Somatic embryogenesis and plant regenraion of Cacao. WO 1993/012645.

Sujatha, M. And Prabakaran, A. J (2003). New ornamental *Jatropha* hybrids through interepecies hybridization. Genetic Resources and Crop Evolution 50:75-82.

Takahashi, et al. (ed). (1991). *Gibberellins*. Springer Verlag, New York.

Trolinder, et al., 1999, Transformation and regeneration of fertile cotton plants. U.S. Pat. No. 5,986,181.

Tuli, R. and Mithilesh, K. (2005). A tissue culture process for production of cotton. WO 2005/063002.

Velten, J. et al. (1984). Isolation of a dual plant promoter fragment from the Ti plasmid of *Agrobacterium tumefaciens*. *EMBO J* 3:2723-2730.

Wilde, H. D. et al. (1992). Expression of foreign genes in transgenic yellow-poplar plants. *Physiol* 98:114-120

Xie, D. and Hong, Y. (2004). Somatic embryogenic regeneration of *Acacia mangium*. U.S. Pat. No. 6,673,608.

What is claimed is:

1. A method for regenerating fertile plants of the genera *Jatropha* through somatic embryogenesis and a two step induction process with callus formation comprising:

(a) culturing an explant of the genera *Jatropha* on a solid hormone-containing medium for a period sufficient to initiate calli growth, wherein the hormone is 2,4-dichlorophenoxyacetic acid (2,4-D) at a concentration of from about 0.5 mg/l to about 10 mg/1;
(b) culturing the explant or calli on a hormone-free medium for a period sufficient to develop somatic embryos or embryogenic calli;
(c) culturing the somatic embryos or embryogenic calli on a solid medium or in a liquid medium to propagate the somatic embryos or embryogenic calli, wherein the liquid medium contains 2,4-D in an amount from about 0.1 mg/l to about 0.5 mg/1;
(d) culturing the somatic embryos on a solid maturation medium for a period of time sufficient to mature the somatic embryos, wherein the maturation medium contains from about 10 g/l to about 20 g/l sucrose or from about 20 g/l to about 60 g/1 maltose; and
(e) culturing the matured somatic embryos on a germination medium for a period of time sufficient to germinate the somatic embryos to produce plantlets, wherein the germination medium contains giberellic acid ($GA_3$) at a concentration of from about 0.5 mg/l to about 5 mg/l.

2. The method of claim 1 which further comprises after step (e) the step of (f) further developing roots of the plantlets on a medium, acclimatizing the plantlets in a soil pot and growing the plantlets into flowering plants.

3. The method of claim 1, wherein the explant is selected from the group consisting of an immature zygotic embryo, a somatic embryo, hypocotyl and root apex tissue.

4. The method of claim 1, wherein the the concentration of the 2,4-D in the hormone-containing medium is from about 2 mg/l to about 5 mg/l.

5. The method of claim 1, wherein the hormone-free medium contains nitrate salts.

6. The method of claim 1, wherein the hormone-free medium is free of $NH_4NO_3$.

7. The method of claim 1, wherein the hormone-free medium is supplemented with one or more amino acids.

8. The method of claim 1, wherein the concentration of the $GA_3$ in the germination medium is from about 1 mg/l to about 4 mg/l.

9. The method of claim 1, wherein the explant and calli are transformed with a DNA construct.

10. The method of claim 1, wherein said liquid medium contains 2,4-D at a concentration of from about 0.2 mg/l to about 0.3 mg/l.

11. The method of claim 1, wherein the liquid medium contains one or more amino acids.

12. The method of claim 1, wherein the liquid medium contains from about 0.5 g/l to about 3.8 g/l $KNO_3$.

13. The method of claim 1, wherein the liquid medium is $NH_4NO_3$-free.

14. The method of claim 1, wherein the liquid medium contains polyethylene glycol (PEG).

15. The method claim 1, wherein the plant is *Jatropha curcas*.

16. The method of claim 1, wherein the plant is an artificial hybrid containing substantial amount of genomic DNA of *Jatropha curcas*.

17. The method of claim 7, wherein the one or more amino acids is glutamine in an amount from about 0.2 g/l to about 2 g/l, or
wherein the one or more amino acids is asparagine in an amount from about 0.2 g/l to about 1.5 g/l, or
wherein the one or more amino acids is a combination of (1) glutamine from about 0.25 g/l to about 2 g/l and (2) asparagine from about 0.1 g/l to about 1 g/l.

18. The method of claim 11, wherein the one or more amino acids is glutamine in an amount from about 0.2 g/l to about 2 g/l, or
wherein the one or more amino acids is asparagine in an amount from about 0.2 g/l to about 1.5 g/l, or
wherein the one or more amino acids is a combination of (1) glutamine from about 0.25 g/l to about 2 g/l and (2) asparagine from about 0.1 g/l to about 1 g/l.

19. The method of claim 1, wherein the concentration of the $GA_3$ in the germination medium is from about 2 mg/l to about 3 mg/l.

20. The method of claim 1, wherein the hormone-containing medium comprises combinations of MS salts, B5 salts or FNL salts with either MS vitamins or B5 vitamins.

21. The method of claim 1, wherein the hormone-free medium comprises combinations of MS salts, B5 salts or FNL salts with either MS vitamins or B5 vitamins.

22. The method of claim 1, wherein the maturation medium comprises combinations of MS salts, B5 salts or FNL salts with either MS vitamins or B5 vitamins.

23. The method of claim 5, wherein the hormone-free medium contains from about 0.5 g/l to about 3.8 g/l $KNO_3$.

24. The method of claim 5, wherein the hormone-free medium contains from about 0.95 g/l to about 1.9 g/l $KNO_3$.

25. The method of claim 12, wherein the liquid medium contains from about 0.95 g/l to about 1.9 g/l $KNO_3$.

26. The method of claim 1, wherein the hormone-containing medium further comprises cytokinin at a concentration of from 0.05 mg/l to about 1 mg/l.

* * * * *